United States Patent [19]

Cölln et al.

[11] 4,335,117
[45] Jun. 15, 1982

[54] 1-HYDROXY-2,2,2-TRICHLOROETHANE-THIONOPHOSPHONIC ACID DIMETHYL ESTERS AS INSECTICIDE

[75] Inventors: Reimer Cölln, Wuppertal; Wilhelm Sirrenberg, Sprockhövel; Wolfgang Behrenz, Overath-Steinenbrueck; Wilhelm Stendel, Wuppertal, all of Fed. Rep. of Germany

[73] Assignee: Bayer Aktiengesellschaft, Leverkusen, Fed. Rep. of Germany

[21] Appl. No.: 865,084

[22] Filed: Dec. 27, 1977

Related U.S. Application Data

[63] Continuation of Ser. No. 665,344, Mar. 9, 1976, abandoned.

[30] Foreign Application Priority Data

Mar. 21, 1975 [DE] Fed. Rep. of Germany ....... 2512375

[51] Int. Cl.³ ......................... C07F 9/40; A01N 57/20
[52] U.S. Cl. ..................................... 424/217; 260/950
[58] Field of Search ................. 260/953, 970; 424/217

[56] References Cited

U.S. PATENT DOCUMENTS 2,579,810 12/1951 Fields ............................. 260/953 X
3,862,277 1/1975 Sirrenberg et al. ............. 260/970 X

OTHER PUBLICATIONS

Heath, "Organophosphorus Poisons," Pargamon Press, N.Y., (1961), pp. 1 and 2.
Kagan, "Chemical Abstracts", vol. 59, 6759a, 1963.
Senyushkin, "Chemical Abstracts", vol. 81, 34481v, 1974.
Farm Chemicals Handbook 1979, p. 502.

Primary Examiner—Anton H. Sutto
Attorney, Agent, or Firm—Sprung, Horn, Kramer & Woods

[57] ABSTRACT

1-Hydroxy-2,2,2-trichloroethane-thionophosphonic acid dialkyl esters of the formula

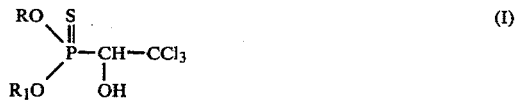

in which
R and $R_1$ each independently is an alkyl radical with 1 to 4 carbon atoms,
which possess arthropodicidal properties.

2 Claims, No Drawings

1-HYDROXY-2,2,2-TRICHLOROETHANE-THIONOPHOSPHONIC ACID DIMETHYL ESTERS AS INSECTICIDE

This is a continuation of application Ser. No. 665,344, filed Mar. 9, 1976, now abandoned.

The present invention relates to and has for its objects the provision of particular new 1-hydroxy-2,2,2-trichloroethane-thionophosphonic acid dialkyl esters, which possess arthropodicidal properties, active compositions in the form of mixtures of such compounds with solid and liquid dispersible carrier vehicles, and methods for producing such compounds and for using such compounds in a new way especially for combating pests, e.g. arthropods, with other and further objects becoming apparent from a study of the within specification and accompanying examples.

It is known from German Pat. No. 977,119 that 1-hydroxy-2,2,2-trichloroethane-phosphonic acid dialkyl esters, for example 1-hydroxy-2,2,2-trichloroethane-phosphonic acid dimethyl ester (Compound A), have a pesticidal, especially an insecticidal, action.

The present invention provides, as new compounds, the 1-hydroxy-2,2,2-trichloroethane-thionophosphonic acid dialkyl esters of the general formula $$\begin{array}{c} RO \\ \diagdown \overset{S}{\underset{\parallel}{P}}-CH-CCl_3 \\ R_1O \diagup \quad \underset{OH}{|} \end{array} \quad (I)$$

in which

R and $R_1$ each independently is an alkyl radical with 1 to 4 carbon atoms.

The compounds of the formula (I) have been found to possess arthropodicidal, especially powerful insecticidal, properties.

Preferably, R and $R_1$ each is a straight or branched alkyl radical with 1 to 3 carbon atoms.

Surprisingly, the 1-hydroxy-2,2,2-trichloroethane-thionophosphonic acid dialkyl esters according to the invention exhibit a substantially greater insecticidal action, coupled with very low toxicity to warm-blooded animals, than the 1-hydroxy-2,2,2-trichloroethane-phosphonic acid dialkyl esters of the same type of action, known from the state of the art. The compounds according to the invention thus represent an enrichment of the art.

The present invention also provides a process for the preparation of a 1-hydroxy-2,2,2-trichloroethane-thionophosphonic acid dialkyl ester of the formula (I), in which a thionophosphorous acid dialkyl ester of the general formula $$\begin{array}{c} RO \\ \diagdown \overset{S}{\underset{\parallel}{P}}-H, \\ R_1O \diagup \end{array} \quad (II)$$

in which

R and $R_1$ have the above-mentioned meanings, is reacted with chloral, of the formula $$O=CH-CCl_3 \quad (III)$$

in the presence of a basic catalyst and optionally in the presence of an inert solvent.

If, for example, thionophosphorous acid dimethyl ester and chloral are used as starting materials, the course of the reaction can be represented by the following equation:

$$\begin{array}{c} CH_3O \\ \diagdown \overset{S}{\underset{\parallel}{P}}-H + O=CH-CCl_3 \\ CH_3O \diagup \\ \quad (IIa) \quad\quad (III) \end{array} \quad (1)$$

$$\xrightarrow{\text{(basic catalyst)}} \begin{array}{c} CH_3O \\ \diagdown \overset{S}{\underset{\parallel}{P}}-CH-CCl_3 \\ CH_3O \diagup \quad \underset{OH}{|} \end{array}$$

The thionophosphorous acid dialkyl esters (II) to be used as starting materials are known and can be prepared in accordance with customary processes (see, for example, German Published Specification DOS No. 1,768,503).

The following may be mentioned as examples of such thionophosphorous acid dialkyl esters: thionophosphorous acid dimethyl ester, diethyl ester, dipropyl ester, diisopropyl ester and dibutyl ester, and also thionophosphorous acid methyl ethyl ester, methyl propyl ester, methyl isopropyl ester, methyl butyl ester, ethyl propyl ester, ethyl isopropyl ester, ethyl butyl ester and propyl butyl ester.

The preparation of the new compounds (I) is preferably carried out in the presence of a suitable solvent or diluent. Practically all inert organic solvents can be used for this purpose, especially aliphatic and aromatic, optionally calorinated, hydrocarbons, such as benzene, toluene, xylene, benzine, methylene chloride, chloroform, carbon tetrachloride and chlorobenzene, ethers, for example diethyl ether, dibutyl ether and dioxane, and also nitriles, such as acetonitrile and propionitrile.

A whole range of basic compounds can be used as catalysts for carrying out the reaction. Aliphatic, aromatic and heterocyclic amines, for example triethylamine, dimethylaniline, dimethylbenzylamine and pyridine, have proved particularly suitable, as have inorganic basic compounds such as alkali metal hydroxides and alkali metal carbonates.

The reaction temperatures can be varied within a fairly wide range. In general, the reaction is carried out at between $-20°$ and $+80°$ C., preferably at about $0°$ to $30°$ C.

The reaction is in general carried out under normal pressure.

To carry out the process, the thionophosphorous acid dialkyl ester and chloral are employed in equimolar amounts, while the basic catalyst is added in an amount which can be between about 2 and 10 mole percent based on the ester.

The reaction is preferably carried out in the presence of one of the above-mentioned solvents, at the stated temperatures. After stirring for a little while, the reaction mixture is repeatedly washed with water, dried and freed from the solvent under reduced pressure. The compounds according to the invention are obtained in the form of oils and can be distilled. They are characterized by their boiling point and refractive index.

The new 1-hydroxy-2,2,2-trichloroethane-thionophosphonic acid dialkyl esters are distinguished by an activity against arthropods, especially by an excellent insecticidal activity, and a favorable level of toxicity to warm-blooded animals. In part, they also exhibit a herbicidal action.

The compounds according to the invention can be employed successfully as pesticides in the hygiene field and against ectoparasites in the veterinary field.

When used against pests harmful to health and pests of stored products, the active compounds are distinguished by an excellent residual action on wood and clay, as well as a good stability to alkali on limed substrates.

The active compounds according to the invention are well tolerated by plants and can be used for combating all or individual stages of development, including the preembryonic, normally sensitive and resistant, stages of development of arthropods where these are known as pests in agriculture, in forestry, in the protection of stored products and materials, and in hygiene.

The economically important pests in agriculture and forestry, as well as pests of stored products, pests destructive of materials and pests harmful to health, include: from the class of the Isopoda, for example, *Oniscus asellus, Armadillidium vulgare* and *Porcellio soaber;* from the class of the Diplopoda, for example, *Blaniulus guttulatus;* from the class of the Chilopoda, for example, *Geophilus carpophagus* and Scutigera spec.; from the class of the Symphyla, for example, *Scutigerella immaculata;* from the class of the Arachnida, for example, *Scorpio maurus* and *Latrodectus mactans;* from the order of the Acarina, for example, *Acarus siro, Argas reflexus, Ornithodoros moubata, Dermanyssus gallinae, Eriophyes ribis, Phyllocoptruta oleivora, Boophilus microplus, Rhipicephalus evertsi, Sarcoptes scabiei,* Tarsonemus spec., *Bryobia praetiosa, Panonychus citri, Panonychus ulmi, Tetranychus tumidus* and *Tetranychus urticae;* from the order of the Thysanura, for example, *Lepisma saccharina;* from the order of the Collembola, for example, *Onychiurus armatus;* from the order of the Orthoptera, for example, *Blatta orientalis, Periplaneta americana, Leucophaea maderae, Blattella germanica, Acheta domesticus,* Gryllotalpha spec., *Locusta migratoria migratoriodes, Melanoplus differentialis* and *Schistocerca gregaria;* from the order of the Dermaptera, for example, *Forficula auricularia;* from the order of the Isoptera, for example, Reticulitermes spec.; from the order of the Anoplura for example, *Phylloxera vastatrix,* Pemphigus spec., and *Pediculus humanus corporis;* from the order of the Thysanoptera, for example, *Hercinothrips femoralis* and *Thrips tabaci;* from the order of the Heteroptera, for example, Eurygaster spec., *Dysdercus intermedius, Piesma quadrata, Cimex lectularius, Rhodnius prolixus* and Triatoma spec., from the order of the Homoptera, for example, *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae, Myzus cerasi, Myzus persicae, Phorodon humuli, Rhopalosiphum padi,* Empoasca spec., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spec., and Psylla spec.; from the order of the Lspidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spec., *Bucculatrix thurberiella, Phyllocnistis citrella,* Agrotis spec., Euxoa spec., Feltia spec., *Earias insulana,* Heliothis spec., *Laphygma exigua, Mamestra brassicae, Panolis flammea, Prodenia litura,* Spodoptera spec., *Trichoplusia ni, Carpocapsa pomonella,* Pieris spec., Chilo spec., *Pyrausta nubilalis, Ephestia kuhniella, Galleria mellonella, Cacoecia podana, Capua reticulana, Choristoneura fumiferana, Clysia ambiguella, Homona magnanima* and *Tortrix viridana;* from the order of the Coleoptera, for example, *Anobium punctatum, Rhizopertha dominica, Bruchidius obtectus, Hylotrupes bajulus, Agelastica alni, Leptinotarsa decemlineata, Phaedon cochleariae,* Diabrotica spec., *Psylliodes, chrysocephala, Epilachna varivestis,* Atomaria spec., *Oryzaephilus surinamensis,* Anthonomus spec., Sitophilus spec., *Otiorrhynchus sulcatus, Cosmopolites sordidus, Ceuthorrhynchus assimilis, Hypera postica,* Dermestes spec., Trogoderma spec., Anthrenus spec., Attagenus spec., Lyctus spec., *Meligethes aeneus,* Ptinus spec., *Niptus hololeucus, Gibbium psylloides,* Tribolium spec., *Tenebrio molitor,* Agriotes spec., Conoderus spec., *Melolonths melolontha, Amphimallus solstitialis* and *Costelytra zealandica;* from the order of the Hymenoptera, for example, Diprion spec., Hoplocampa spec., Lasius spec., *Wonemorium pharaonis* and Veapa spec.; from the order of the Diptera, for example Aëdes spec., Anopheles spec., Culex spec., *Drosophila melanogaster, Musca domestica,* Fannia spec., *Stomoxys calcitrans,* Hypoderma spec., *Bibio hortulanus,* Oscinella frit, Phorbia spec., *Pegomyia hyoscyami, Calliphora erythrocephala,* Lucilia spec., Chrysomyia spec., *Ceratitis capitata, Dacus oleae* and *Tipula paludosa;* and from the order of the Siphonaptera, for example *Xenopsylla cheopis.*

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as Freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other insecticides and acaricides, or nematocides, fungicides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–10%, preferably 0.01–1%, by weight of the mixture. Thus, the present invention contemplates overall compositions which comprise mixtures of a conventional dispersible carrier vehicle such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combating or controlling pests, e.g. arthropods, and more particularly methods of combating insects, which comprises applying to at least one of correspondingly (a) such arthropods and (b) the corresponding habitat thereof, i.e. the locus to be protected, e.g. to a growing crop, to an area where a crop is to be grown or to a domestic animal, a correspondingly combative or toxic amount, i.e. an arthropidicidally effective amount, of the particular active compound of the invention alone or together with a carrier vehicle as noted above. The instant formulations or compositions are applied in the usual manner, for instance spraying, atomizing, vaporizing, scattering, dusting, watering, squirting, sprinkling, pouring, fumigating, dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

$LD_{100}$ test
Test insects: *Sitophilus granarius*
Solvent: Acetone 2 parts by weight of the active compound were taken up in 1,000 parts by volume of the solvent. The solution so obtained was diluted with further solvent to the desired concentrations.

2.5 ml of the solution of the active compound were pipetted into a Petri dish. On the bottom of the Petri dish there was a filter paper with a diameter of about 9.5 cm. The Petri dish remained uncovered until the solvent had completely evaporated. The amount of active compound per $m^2$ of filter paper varied with the concentration of the solution of active compound. About 25 test insects were then placed in the Petri dish and it was covered with a glass lid.

The condition of the test insects was observed 3 days after the commencement of the experiments. The destruction, in %, was determined. 100% denotes that all of the test insects had been killed; 0% denotes that no test insects had been killed.

The active compounds, the concentrations of the active compounds, the test insects and the results can be seen from the following table:

TABLE 1

| ($LD_{100}$ Test/*Sitophilus granarius*) | | |
|---|---|---|
| Active compound | Active compound concentration in the solution, in % | Degree of destruction in % |
| $(CH_3O)_2\overset{\overset{\displaystyle O}{\|}}{P}-\underset{\underset{\displaystyle OH}{\|}}{CH}-CCl_3$ (known) (A) | 0.2<br>0.02 | 100<br>15 |
| $(CH_3O)_2\overset{\overset{\displaystyle S}{\|}}{P}-\underset{\underset{\displaystyle OH}{\|}}{CH}-CCl_3$ (1) | 0.2<br>0.02<br>0.002 | 100<br>100<br>50 |

EXAMPLE 2

Residual Test

Test insects: *Musca domestica* and *Aedes aegypti*

Wettable powder base consisting of:
3% of sodium diisobutylnaphthalene-1-sulfonate
6% of sulfite waste liquor, partially condensed with aniline
40% of highly dispersed silicic acid, containing CaO
51% of colloidal kaolin To produce a suitable preparation of the active compound, 1 part by weight of the active compound was intimately mixed with 9 parts by weight of the wettable powder base. The spray powder thus obtained was suspended in 90 parts of water.

The suspension of the active compound was sprayed, in an amount of, for example, 1 g of the active compound per m², onto substrates consisting of different materials.

The sprayed coatings were, at specific intervals of time, tested for their biological activity.

For this purpose, the test insects were placed on the treated substrates. There was put over the test insects a squat cylinder which was closed at its upper end with a wire mesh in order to prevent the insects from escaping. After the insects had spent 8 hours on the substrate, the destruction of the test insects was determined in %. 100% denotes that all test insects had been killed; 0% denotes that none of the test insects had been killed.

The active compounds, their amounts, the nature of the substrates and the results can be seen from the following table:

TABLE 2

(Residual Test/*Musca domestica* and *Aedes aegypti*)

| Active compound | Test substrates | Test insects | Destruction of the test insects in % after hours (hrs) | | | | | |
|---|---|---|---|---|---|---|---|---|
| | | | 1 | 2 | 4 | 6 | 10 | 12 weeks |
| $(CH_3O)_2\overset{\overset{O}{\|\|}}{P}-\underset{\underset{OH}{\|}}{CH}-CCl_3$ (known) (A) | Plywood Clay Clay + Lime | *Aedes aegypti* *Aedes aegypti* *Musca domestica* | $5\frac{1}{2}^{hrs}=100$ | | $8^{hrs}=0$ | | | $8^{hrs}=40$ |
| $(CH_3O)_2\overset{\overset{S}{\|\|}}{P}-\underset{\underset{OH}{\|}}{CH}-CCl_3$ (1) | Plywood Clay Clay + Lime | *Aedes aegypti* *Aedes aegypti* *Musca domestica* | $1\frac{1}{2}^{hrs}=100$ | | | $6^{hrs}=100$ | $7\frac{1}{2}^{hrs}=100$ | |

EXAMPLE 3

Test with parasitic fly larvae

Solvent: 35 parts by weight of ethylene polyglycol monomethyl ether
35 parts by weight of nonylphenol polyglycol ether To produce a suitable preparation of active compound, 30 parts by weight of the active substance in question were mixed with the stated amount of solvent which contained the above-mentioned proportion of emulsifier and the concentrate thus obtained was diluted with water to the desired concentration.

About 20 fly larvae (*Lucilia cuprina*) were introduced into a test tube which contained approximately 2 cm³ of horse muscle. 0.5 ml of the preparation of active compound was applied to this horse meat. After 24 hours, the degree of destruction in % was determined. 100% means that all the larvae had been killed and 0% means that no larvae had been killed.

The active compounds investigated, the concentrations of the active compounds used and the results obtained can be seen from the table which follows:

TABLE 3

(Test with parasitic fly larvae/*Lucilia cuprina* res.)

| Active compound | Active compound concentration in ppm | Degree of destruction in % |
|---|---|---|
| 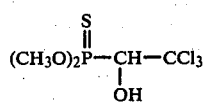 (1) | 100 30 10 3 | 100 100 100 0 |

The process of this invention is illustrated by the following preparative Examples.

EXAMPLE 4

$$(CH_3O)_2\overset{\overset{S}{\|\|}}{P}-\underset{\underset{OH}{\|}}{CH}-CCl_3 \quad (1)$$

750 g (5.07 moles) of chloral were allowed to run into a mixture of 631 g (5 moles) of thionophosphorous acid dimethyl ester, 2 l of toluene and 10 g of triethylamine over the course of 25 to 30 minutes while stirring and applying external cooling, the internal temperature being 15°–20° C. After stirring for a further hour at 20° C., the mixture was washed once with very dilute hydrochloric acid and then repeatedly with water, until the wash water reacted neutral. The organic phase was dried over sodium sulfate, treated with a little active charcoal and then freed from the solvent under reduced pressure. 1,330.5 g (97.4% of theory) of 1-hydroxy-2,2,2-trichloroethane-thionophosphonic acid dimethyl ester remained as a colorless oil of refractive index $n_D^{22}$: 1.5338. The product could be distilled in vacuo and had a boiling point of 116° C./2 mm Hg.

EXAMPLE 5

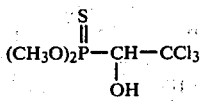 (1)

0.33 g of potassium hydroxide powder (86% strength) was added to a mixture of 12.6 g (0.1 mole) of thionophosphorous acid dimethyl ester and 100 ml of toluene at 10° C. After 5 minutes, 14.8 g (0.1 mole) of chloral, dissolved in 50 ml of toluene, were added dropwise while stirring and applying external cooling, the internal temperature being 10° to 15° C. The reaction mixture was stirred for a further hour at 50° C. After adding 3 g of kieselguhr, the solid products were filtered off at the pump. The filtrate, after washing with water and evaporating the solvent under reduced pressure, gave 24.2 g (89% of theory) of 1-hydroxy-2,2,2-trichloroethane-thionophosphonic acid dimethyl ester.

EXAMPLE 6

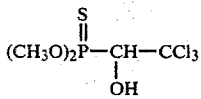 (1)

The same procedure as in Example 5 gave 24.3 g (89% of theory) of 1-hydroxy-2,2,2-trichloroethane-thionophosphonic acid dimethyl ester when 0.7 g of potassium carbonate powder was used in place of the potassium hydroxide.

EXAMPLE 7

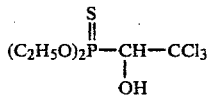 (2)

74.2 g (0.5 mole) of chloral were added dropwise over the course of 10 to 15 minutes to a mixture of 77.1 g (0.5 mole) of thionophosphorous acid diethyl ester, 200 ml of toluene and 1 g of triethylamine while stirring and applying external cooling, the internal temperature being 15° to 20° C., and the reaction mixture was then stirred for 30 minutes at 25° C. After working up, which took place as in Example 4, 143.4 g (95% of theory) of 1-hydroxy-2,2,2-trichloroethane-thionophosphonic acid diethyl ester were obtained in the form of a colorless oil which had a boiling point of 104° C./0.4 mm Hg and a refractive index $n_D^{21}$ of 1.5104.

It will be appreciated that the instant specification and examples are set forth by way of illustration and not limitation, and that various modifications and changes may be made without departing from the spirit and scope of the present invention.

What is claimed is:

1. The compound 1-hydroxy-2,2,2-trichloroethane-thionophosphonic acid dimethyl ester of the formula

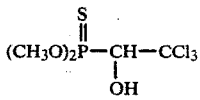

having a boiling point of 116° C./2 mm Hg.

2. A method of combating arthropods which comprises applying to the arthropods or an arthropod habitat an arthropodicidally effective amount of a compound according to claim 1.

* * * * *